United States Patent [19]

Buckley

[11] 4,200,921
[45] Apr. 29, 1980

[54] APPARATUS AND METHOD WHEREBY WAVE ENERGY IS CORRELATED WITH POSITIONAL RELATIONSHIPS IN A SYSTEM

[75] Inventor: Bruce S. Buckley, Cambridge, Mass.

[73] Assignee: Massachusetts Institute of Technology, Cambridge, Mass.

[21] Appl. No.: 911,622

[22] Filed: Jun. 1, 1978

Related U.S. Application Data

[62] Division of Ser. No. 679,262, Apr. 22, 1976, Pat. No. 4,095,475.

[51] Int. Cl.² ............................................. G01S 9/66
[52] U.S. Cl. ................................... 367/87; 343/12 R
[58] Field of Search ...................... 340/1 R; 343/12 R

[56] References Cited

U.S. PATENT DOCUMENTS

| | | | |
|---|---|---|---|
| 3,199,103 | 8/1965 | Augustine | 343/12 R |
| 3,500,301 | 3/1970 | Meier | 340/1 R |
| 3,622,957 | 11/1971 | Libengood et al. | 340/1 R |
| 3,944,963 | 3/1976 | Hively | 340/1 R |
| 3,973,259 | 8/1976 | Hellgren et al. | 343/12 R X |

Primary Examiner—T. H. Tubbesing
Attorney, Agent, or Firm—Arthur A. Smith, Jr.; Robert Shaw

[57] ABSTRACT

A way of automatically inspecting a machined part, for example, to a tolerance of 0.001 inches. A minicomputer monitors a change in phase, for example, of wave energy impinging upon a sample part and compares it with a change in phase of such energy for a standard or master part, any difference between the monitored changes being interpreted to determine if the sample is within acceptable tolerance limits. The inspection approach described uses no moving parts and can be used to inspect many dimensions of a part simultaneously in less than a second. Acoustic waves or microwave electromagnetic wave energy can be used to inspect parts of any shape. The inspection system disclosed can be used, as well, to monitor the geometry of an object over time to note any changes in said geometry. And the concepts of the inspection system can be employed in conjunction with robot-controlled devices to provide close-positioning data for such devices.

5 Claims, 7 Drawing Figures

APPARATUS AND METHOD WHEREBY WAVE ENERGY IS CORRELATED WITH POSITIONAL RELATIONSHIPS IN A SYSTEM

This is a division of Ser. No. 679,262 (now U.S. Pat. No. 4,095,475), filed Apr. 22, 1976 and is filed to comply with a requirement for restriction.

The present invention relates to inspection apparatus and method wherein a sample manufactured part is compared with a standard or master part by impinging wave energy on the standard or master part and deriving information from wave energy reflected from the part, which information is employed to establish a standard against which the sample is compared; it also relates to systems wherein the geometry of a single obect is monitored over time and to a system to provide fine-tuning positioning information.

There accompanies herewith a copy of a writing by the present inventor entitled "Phase Monitored Inspection"; the writing is hereby incorporated herein by reference and it is drawn upon heavily for the text that now follows.

Inspection today is one of the least automated of manufacturing operations which range from simple hand operations to direct numerical control processes (computer controlled tools). Automated inspection covers the entire gamut of sophistication from hand micrometer inspection to very sophisticated automated inspection stations. However, most shop practice is with hand-operated inspection equipment: very little automation has worked its way into the inspection process.

Automated inspection has been applied most successfully to large production runs. For example, in the manufacture of automobile connecting rods, precision inspection of the machined surfaces is automatic. Because of the large number of nearly identical parts, economics dictate an inspection "transfer line". The inspecting machine is specially designed for each part shape and is generally not computer controlled. While effective for large production runs ($10^6$ parts or more), these techniques are uneconomic for low volume inspection.

Computer controlled inspection machines are most commonly used in automating low production runs. The simplest of these machines has a probe which is brought into contact with various surfaces of the part to be inspected. The part is usually jigged and the probe is positioned by hand. As the probe is touched to various surfaces, a digital readout of the probe's position leads indirectly to the part dimensions. The next level of sophistication interfaces a computer to calculate directly the dimensions of the part from the probe's position. The most highly sophisticated inspection machines position the probe under computer of tape control. These are numerically controlled vertical milling machines: the milling machine positions a spinning cutter while the inspection machine positions an inspection probe. Both must be very rigid to minimize stiffness errors. In a numerically-controlled inspection machine, the probe can be positioned with as many as five degrees of freedom with respect to the machine parts.

Accuracy is an important performance criterion for automated inspection machines. Parts can be inspected to tolerances as small as a 0.0001 inch (2.54 microns), although most machines are somewhat less accurate—0.001 inch (25.4 microns) is typical. Probes which actually contact the part's surface are subject to wear, so non-contact probes are sometimes used. Optical, pneumatic and electronic probes can all measure as accurately as the probe can be positioned, and the part inspected has a maximum dimension on the order one inch to ten inches. Parts whose maximum dimension is either much larger or much smaller than this must be inspected by hand or by specialized inspection machines. However, the vast bulk of machined parts are in this category.

The primary problem of current automated inspection machines is their inability to measure dimensions from a distance. To measure a ten inch part to an accuracy of 0.001 inches (25.4 microns) requires a sensor accurate to one part in 10,000. But this is an order of magnitude greater than the best conventional techniques. For example, optical ranging devices can measure to 0.01 inch (254 microns) from several feet, and electrical sensors can measure to accuracies of 0.0001 inch (2.54 microns) but only from distances of about 0.1 inch (0.00254 m). No method is suitable for inspecting from a distance—both 0.001 inch (25.4 microns) accuracy and 10 inch (0.254 m) standoff. Conventional automated inspection machines circumvent this deficiency by moving the sensing probe close to the machined part. Thus, inspecting machines are complicated moving-part devices subject to frequent breakdowns if not properly maintained.

Inspection speed is the second important performance criterion of an automated inspection machine. Inertial forces on the massive structure of the inspecting machine prevent rapid inspection. A computer controlled inspecting machine can measure about one dimension a second. Since the various dimensions of a part must be inspected serially (i.e., one dimension after the other) the net result is that even with computer controlled inspection machines inspection is a time-consuming operation.

Research is being done in several methods to allow rapid inspection from a distance. Electronically manipulated video signals are a low resolution approach. Another intriguing method uses defocused holograms to optically inspect parts. An electronic representation of the holograms is processed to yield dimensional information. Although these techniques appear promising, they have not yet been perfected.

Automated inspection must be viewed with a perspective toward its ultimate use: automated manufacturing or, more specifically, Computer Managed Parts Manufacturing (CMPM) which uses computers to automate the operation of an entire manufacturing plant. Simulations of CMPM systems—few have been built—show that a random part mix gives a many-fold increase in productivity. The most efficient operation is not associated with many identical parts which tie up a single machine in the automated factories. Only when all the parts being manufactured simultaneously are substantially different from one another can the true benefits of automated manufacturing be realized.

In a CMPM facility, the parts to be machined are transported on moving pallets. The pallets holding the workpiece can be positioned at each machining station with high accuracy. The palleted workpieces are shuttled by conveyors from one machining station to another under computer control; human operators are required only for monitoring and initial fixturing. The productivity of a CMPM system is substantially increased by (1) 24-hour operation; (2) high utilization of machine tools; (3) elimination of delays between machine operations; (4) elminination of errors by computer management. Inspection is one of the most critical aspects of a CMPM system. When huge factories are automated, malfunction must be recognized very quickly before errors propagate through the entire system. Usually the machined parts cannot wait until their completion to be inspected; they must be periodically inspected through the various machining operations. Hence, more inspection stations are required with more reliance on the results in a CMPM system than in a conventional parts manufacturing factory.

Two types of inspection are required: gross error inspection and dimension inspection. A typical gross error is identifying when a drill bit has been broken off in a partially machined part. Quick error identification is important not only because the bit cannot be used for further drilling, but also because subsequent operation on the part will destroy other cutters. Normally, gross errors are found by the machinist, during or between the machining operations. Since this is not possible on a CMPM system, gross error inspection should be performed after each machining operation. Dimension inspecting, on the other hand, is the high accuracy inspecting of a part's dimension. Generally a part is dimension inspected only after machining is completed. This final inspection can be used for quality control as well as monitoring tool wear of the various machining operations. Gross error inspecting, then, is low accuracy measurements repeated often, while dimension inspecting is a high accuracy process done seldom.

An automated inspection system to be used in a CMPM system should be capable of inspecting both gross errors and dimensions. The system must accept random part shapes and random sequences. Inspection must be both rapid and accurate. Furthermore, the system should be inexpensive; many inspection stations will be needed in a CMPM system.

Accordingly, an object of the present invention is to provide a method of inspection and apparatus therefor whereby random-shaped parts can be inspected quickly and with acceptable accuracy without need to effect actual physical contact with the part.

Another object is to provide an inspection system in which many identical parts of similar shape can be quickly inspected with regard to geometry.

Still another object is to provide an inspection system that can be used in CMPM-type operations but which is useful, as well, in facilities of a more conventional nature, but facilities having high volume production of similar parts.

In an automatic operation there is need for means to inspect cutting tools and the like to note any deterioration thereof in the course of operation. Accordingly, a further object is to provide an inspection system where, for example, a cutting tool or the like is periodically inspected, automatically, to note any changes in the geometry thereof as a consequence of usage.

Also, use of automatic assembly equipment is hampered somewhat because of the costly approach now needed to permit final and smaller positioning changes in such equipment. Thus, a still further object is to provide an automatic inspection system which permits feedback in a robot-controlled operation for exact robot manipulation to effect final positioning and similar operations.

These and still further objects are addressed in the description hereinafter.

The foregoing objects are achieved in a method of inspecting manufactured parts and the like or a method of exact positioning of robot-controlled machines, which employs wave energy that is impinged upon and reflected by the part, the wavelength of the energy significantly greater than the optical band in the electromagnetic spectrum and, indeed, being ideally substantially larger by an order of magnitude than the tolerances to-be-sensed of the part to-be-inspected (e.g., the ratio of tolerances to wavelength being typically about 1/100). The wave energy at a single frequency is directed upon a sample part or object which reflects the same. The reflected wave energy is detected and a characteristic of the reflected energy is compared with the same characteristic of a standard or master part similarly treated to note any differences $\theta_\Delta$ therebetween; the difference $\theta_\Delta$ must be within acceptable tolerance in an inspection system. Or the characteristic of the reflected wave energy is compared with some other wave pattern and information derived from the comparison is used to effect close positioning of the robot-controlled machine. The wave energy used may be acoustic energy or microwave electromagnetic energy and the characteristic of the energy used for comparison is preferably the phase difference between the reflected wave and the original wave that is directed upon the particular part.

The invention is hereinafter described with reference to the accompanying drawing in which:

FIG. 5 is an isometric view of a modification of the inspection system of FIG. 1 and shows a small portion of a turret lathe with an inspection system of the present invention to monitor cutter wear, breakage and the like;

The present invention is multi-faceted; it applies to a parts inspection system to permit automatic inspection of many like parts; it applies to periodic, and automatic, inspection of the same object such as a cutting tool or the like to detect geometric changes in the object; and it applies to a positioning system to permit small, but accurate, positioning corrections. Most of this specification is devoted to the parts inspection system, but the other aspects are gone into in some detail.

The invention is describe here in greatest detail with reference to an acoustic system, but, as noted, microwave electromagnetic wave energy can also be used. The description is first of a general nature and then more specific, the latter being with reference to an actual system built and used to show the efficacy of the present concepts.

Referring now to the figures, apparatus for inspecting manufactured parts and the like is shown at 101 in FIG.

Figure 1:
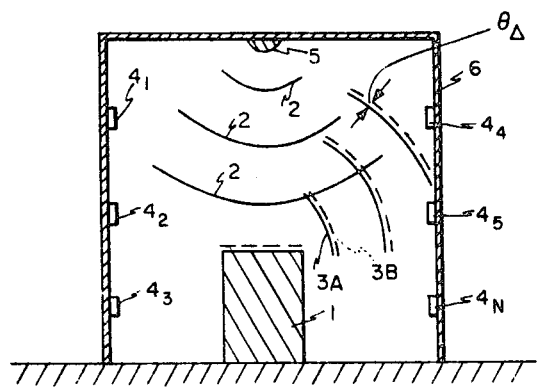
FIG. 1 is a side section view of a schematic representation of a portion of an inspection system that employs the present concepts and shows, among other things, a chamber, microphones and a speaker.
Figure 2:
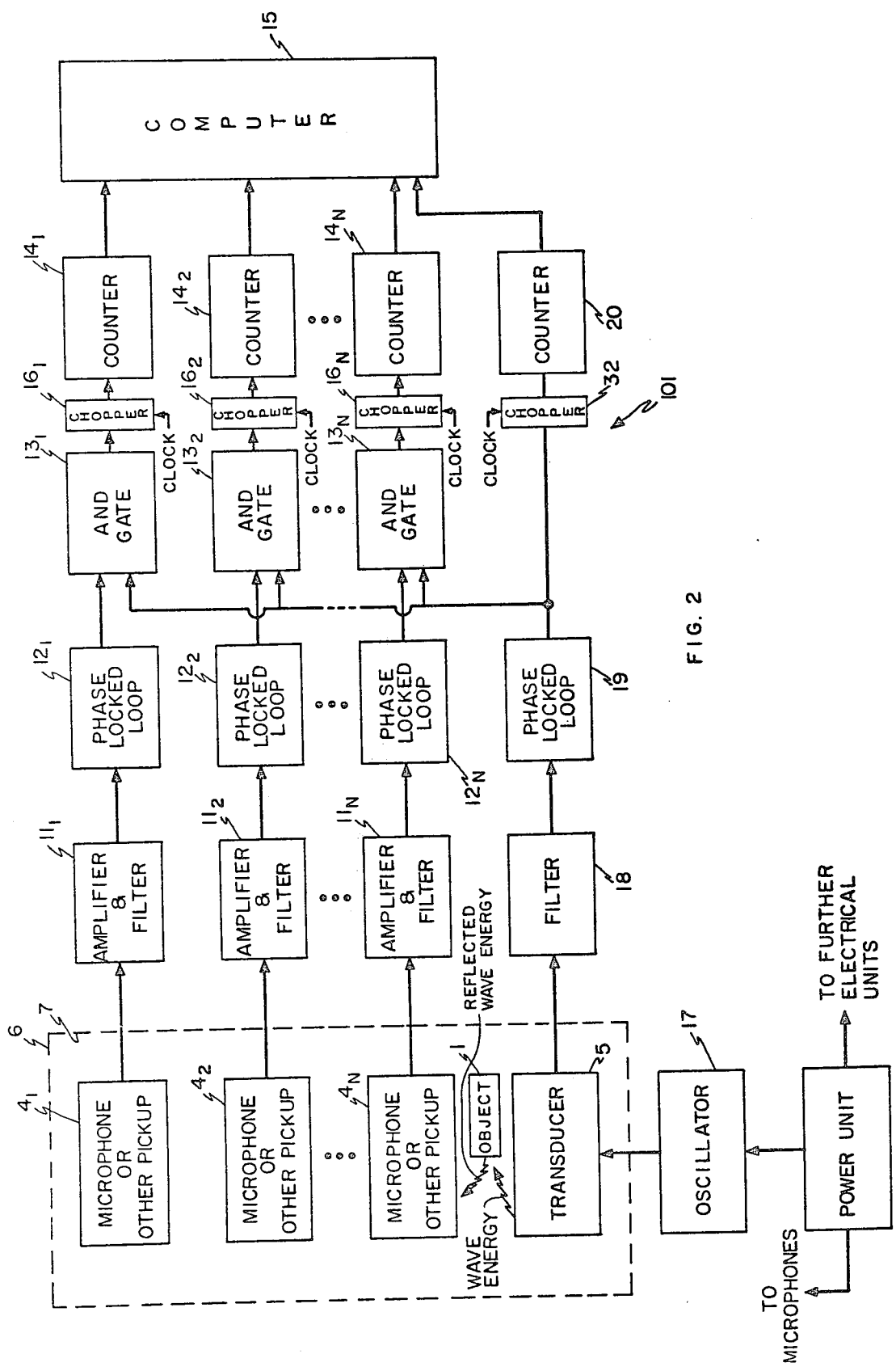
FIG. 2 is a schematic representation, block diagram in form, of an inspection system of the present invention.

2; the system 101 is acoustic. In FIG. 1 the object labeled 1 is a standard or master part, but it is, for present purposes, a sample part (i.e., a part to-be-inspected), as well, that is, in actual apparatus the system 101 is calibrated using a standard part and, then, the sample part replaces the standard. The solid outer lines of the object 1 represent the dimensions of the standard and the broken upper line represents a sample that has a slightly larger height than the standard, but the same width. Acoustic wave energy as represented by lines 2 is directed upon the object 1 and reflected therefrom. The reflected acoustic wave energy is labeled 3A and 3B (the later being dotted) to represent the energy reflected wave energy from the standard part and the sample part, respectively. The space between the waves 3A and 3B represents a phase shift differential and is indicated to be such; that phase shift differential is detected and recorded, as hereinafter explained, and is represented by the designation $\theta_\Delta$ hereinafter. The original wave energy 2 is emitted by an acoustic transducer 5 which may be a speaker and the energy is at a single wavelength. In the preferred form of the invention, the phase of the reflected wave energy 3A is compared with the original wave energy 2 and any phase difference $\theta_B$ therebetween is noted to establish an acceptable standard; for inspection purposes, the phase of the reflected wave energy 3B is compared with the original wave energy 2 and any phase difference $\theta_A$ therebetween is compared with the phase difference $\theta_B$ to determine any differential $\theta_\Delta$ therebetween. A maximum value of the differential $\theta_\Delta$ is established as the value that cannot be exceeded for the sample part to be acceptable. Sensing of the reflected waves is effected by wave receivers or microphones $4_1$... The part 1, the transducer 5 and the receivers $4_1$... are all housed within a chamber 6. The emitter or speaker 5 sends out waves of a constant frequency which are reflected from the part 1 and the interior of the chamber 6 and then picked up by the receivers $4_1$... The electrical circuitry to energize the speaker and the microphones, the analyzing circuitry, etc., are shown in FIG. 2 and are discussed later; but first there is an explanation of the concepts underlying the present invention.

As a result of the constant (or single) frequency wave emission, the output of the receivers $4_1$... will be sinusoidal signal of the same frequency as the emitted wave but differing in both amplitude and phase. Inspection of the part 1 is possible by monitoring the phase differences between emitted and received waves, as above indicated and as now explained in detail.

First, a master workpiece or standard part 1 is positioned at the inspecting station and enclosed by the inspection chamber. The phase monitored at each receiver, $4_1 \ldots 4_N$, constitutes the phase vector of the master workpiece:

$$\bar{\theta} = (\theta_1, \theta_2, \ldots \theta_N). \tag{1}$$

A subsequent or sample part to be inspected is positioned at the same point and orientation, and a similar phase vector, $$\bar{\theta}' = (\theta'_1, \theta'_2, \ldots \theta'_N) \tag{2}$$

is monitored for the part. The difference in phase between the master workpiece and the part:

$$\overline{\Delta\theta} = (\theta_1 - \theta'_1, \theta_2 - \theta'_2, \ldots, \theta_N - \theta'_N) \tag{3}$$

can be used to determine whether a sample part is within tolerances, when it is not, and by how much. (In this description and in the appended claims, the designation $\theta_A$ is used to denote any one of the phase vectors or differences $\theta'_1, \theta'_2 \ldots, \theta_B$ is used to denote any one of the phase vectors or differences $\theta_1, \theta_2 \ldots,$ and $\theta_\Delta$ is any differential between $\theta_A$ and $\theta_B$. The major thrust of this specification is the detection of phase differences and comparisons thereof to infer information, be it shape or position, but, as indicated herein, the amplitude or level of the wave energy or some other characteristic thereof can be also used to infer such information and the terms $\theta_A$, $\theta_B$ and $\theta_\Delta$ are intended to embrace the latter as well.) Since automated manufacturing assumes that a part is already mounted on a pallet which can be positioned very accurately, placing the master workpiece and part at the same point and orientation is not difficult.

For gross errors the phase differences may be monitored such that any large change rejects the part, and, indeed, white noise and statistical methods can be used. Dimension inspecting, however, is more difficult. A sensitivity matrix, S, can be determined which gives the sensitivity of each phase difference, $\Delta\theta$, for each dimension tolerance on the part. An on-line multiplication of the phase difference vector ($\overline{\Delta\theta}$) times the inverse of the sensitivity matrix results in a deviation vector:

$$\bar{d} = (d_1, d_2, \ldots d_m). \tag{4}$$

The deviation vector $\bar{d}$ is the amount that each dimension have deviated from that of the master workpiece.

$$\bar{d} = S^{-1} \overline{\Delta\theta}. \tag{5}$$

If any deviation d is outside the tolerance for that dimension, the part is rejected.

The sensitivity matrix assumes linear changes in phase for small deviations: this will be true if the emitted wavelengths is much greater than the largest possible deviation. A one-inch (0.0254 m) wavelength allows deviations as large as 0.010 inch (254 microns) to be measured while still satisfying this criterion. The sensitivity matrix itself is determined by a calibration procedure performed only once for each master workpiece. It involves matching the phase differences ($\overline{\Delta\theta}$) with actual dimensions of parts with high and low tolerance limits. In automated manufacturing, the calibration procedure can be performed under computer control by slightly undercutting or overcutting the various dimensions on the first few parts. Once the sensitivity matrix has been determined, all subsequent parts characterized by the master workpiece can be inspected online. With off-the-shelf hardware, all dimensions can be simultaneously inspected in less than one second.

Two types of waves are suitable for phase monitored inspection: ten kilo-cycle acoustic waves and thirteen gigahertz microwaves. Both have a wavelength about one inch long (0.0254 m) and phase can be measured in both cases to better than one part in three hundred. Ten kilohertz acoustic waves are in the realm of hi-fi equipment. Although equipment is very cheap, acoustic noise, Doppler shift, and changes in acoustic velocity with temperature all combine to make acoustic phase monitored inspection less accurate than microwave systems by an order of magnitude. Microwave systems operating at thirteen gigahertz use readily available police radar components not subject to the noise problems of an acoustic phase monitored inspection system.

The electrical circuitry to accomplish the functions described above is shown in FIG. 2 wherein the chamber 6 is represented by a broken line that encloses he speaker or other transducer 5 and a plurality of microphones or other pickups $4_1 \ldots 4_N$ distributed around the interior of the chamber 6 and operable to detect wave energy reflected from the object 1. The interior surface is coated with or contains therein a material 7 that absorbs wave energy of the type wave used in order to enhance the effect of the reflected wave energy; that is, the ideal situation is one in which the only reflected wave energy that reaches the pickups $4_1 \ldots 4_N$ is that energy which reflects directly from the object 1. Electric signals generated by the pickups $4_1 \ldots 4_N$ are fed to amplifier and filter units $11_1 \ldots 11_N$, respectively, thence to phase locked loops $12_1 \ldots 12_N$, respectively, and thence as one input to AND-gates $13_1 \ldots 13_N$, respectively. Another input to the AND-gates is derived from the transducer 5 through a filter 18 and phase locked loop 19. In this way the output of each AND-gate is a pulse whose width represents a phase difference between the reflected wave energy detected by the particular microphone and the original wave energy directed upon the object 1. The outputs of the AND-gates $13_1 \ldots 13_N$ are respectively connected as inputs to chopper $16_1 \ldots 16_N$ which convert the analog signal from the gates to digital signals, the digital signals being fed to counters $14_1 \ldots 14_N$ whose outputs serve as inputs to a computer 15 which can be a general purpose computer properly programmed or a microcomputer. A chopper 32 is connected to receive a signal from the transducer 5 and provide a digital input to a counter 20 that provides a further input to the computer 15. The computer is programmed to provide a difference signal $\theta_A$ for each microphone (i.e., the signals $\theta_1', \theta_2' \ldots$ before mentioned) by using the respective inputs from the counters $14_1 \ldots$ and comparing each with the input from the counter 20. The computer is further programmed to compare each difference signal $\theta_A$ with a stored difference signal $\theta_B$ (i.e., the signals $\theta_1, \theta_2 \ldots$ before mentioned) and to determine any differential $\theta_\Delta$ (i.e., $\theta_1 - \theta_1', \theta_2 - \theta_2' \ldots$) therebetween. In the present context, the elements $4_1$, $11_1$, $12_1$, $13_1$, $16_1$ and $14_1$, for example interact to detect the reflected wave energy and to develop a signal $\theta_A$ therefrom, which signal bears a relationship to geometrical characteristics of the object 1, and the computer 15 serves to compare the signal $\theta_A$ with a standard signal $\theta_B$ representative of the geometrical characteristics of a standard to determine any differential or vector $\theta_\Delta$ therebetween. The computer can be programmed to establish limits for the difference $\theta_\Delta$ developed by each pickup on a go-no-go basis. Whereas, for very accurate appraisals for inspecting on the basis of small tolerance limits, phase angle is the characteristic of the single-frequency wave energy that should be used, amplitude or some characteristic can be employed and for some situations, very rough information can be derived from random wave energy; the latter situation may be one in which it is important to know if some gross change has occurred in a mechanical part (e.g., a tool is broken and held within the part), which gross change could be a source of difficulty, say, in an automated operation.

Figure 3:
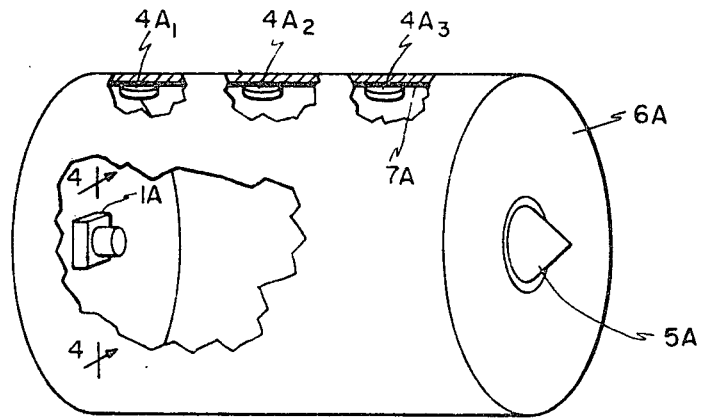
FIG. 3 is an isometric view, partly cutaway, of the same system elements as shown in FIG. 1 but in a slightly different configuration.
Figure 4:
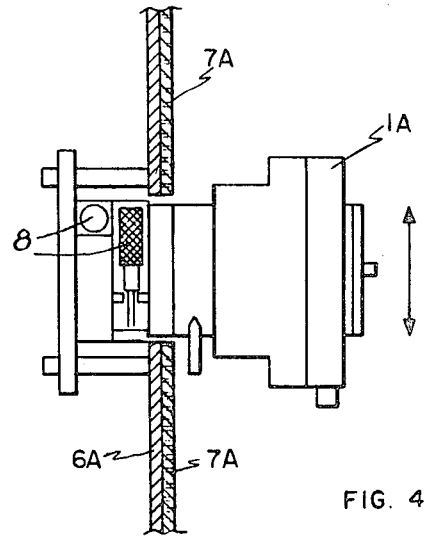
FIG. 4 is a enlarged view taken upon the line 4—4 of FIG. 3 looking in the direction of arrows.

Experimental apparatus was built to verify the feasibility of phase monitored inspection. An acoustic system, while low in accuracy, was chosen because of its low cost, FIGS. 3 and 4 show an inspection chamber at 6A with an associated emitter 5A and receivers $4A_1$, $4A_2 \ldots$ A ten Kc oscillator is used to drive a speaker through an audio amplifier as before (neither is shown in FIGS. 3 and 4). The receivers are microphones attached to the side of the inspection chamber; the interior has an acoustic absorber surface 7A. After suitable amplification, phase differences between the speaker and the microphones are measured with a phase meter. Instead of physically replacing the master with separate parts, as a simplification, the master was moved in two directions (i.e., x and y) by calibrated translation stages 8 which are, in fact, stages used in optical systems for accurate translational movement. To ensure that the results are valid for other than simple part shapes, a very complex workpiece was used: an automobile carburetor which is the object marked 1A.

Moving the carburetor 1A slightly in each of two directions ($\Delta x$, $\Delta y$) caused phase changes ($\Delta\theta_1$, $\Delta\theta_2$) in each of two microphones. The resulting sensitivity matrix for the two microphones, $$S = \begin{bmatrix} \frac{\Delta\theta_1}{\Delta x} & \frac{\Delta\theta_2}{\Delta x} \\ \frac{\Delta\theta_1}{\Delta y} & \frac{\Delta\theta_2}{\Delta y} \end{bmatrix} = \begin{bmatrix} .06 & -.24 \\ .97 & .01 \end{bmatrix}$$

General expression ・ Experimental data is found by taking the partial derivative of the deviations with respect to each microphone's phase difference.

Given the sensitivity matrix, any movement of the carburetor in the x or y direction can be determined by monitoring the phase differences at each microphone. For instance if a change in phase of plus two degrees is noted on both microphones the phase difference vector, $\overline{\Delta\theta}$, will be (2, 2), giving a deviation vector of:

$$\begin{bmatrix} d_1 \\ d_y \end{bmatrix} = S^{-1} \cdot \overline{\Delta\theta} = \begin{bmatrix} .04 & 1.05 \\ -4.26 & .26 \end{bmatrix} \begin{bmatrix} 2.0 \\ 2.0 \end{bmatrix} \approx \begin{bmatrix} 2 \\ -8 \end{bmatrix}$$

Hence the carburetor must have moved two mils (fifty-one microns) in the x direction and minus eight mils (203 microns) in the y direction to be consistent with the phase changes recorded by the microphones. This case was purposely chosen so that one microphone would be sensitive to x movement and the other to y movement. In general this would not be true; both microphones should be sensitive to both x and y movement. By finding the inverse of the sensitivity matrix, the proper linear combination of $\Delta\theta_1$ and $\Delta\theta_2$ can always be found which gives the x or the y movement independently. Usually more receivers (n) than deviations (m) will exist, hence a pseudo-inverse of the S matrix is appropriate.

Phase monitored inspection was shown to be a valid means for inspecting parts of arbitrary shape. The experimental apparatus also shows that an acoustic system is very sensitive to ambient noise, line noise transients, and Doppler effects, limiting accuracy to about two mils (fifty-one microns). However, the acoustic experiments showed that the system is valid for gross error inspection, as well as for dimension inspection indicating both where a part is out of tolerance and by how much.

Automated inspection, as above noted, is currently done by a point-by-point inspecting machine. These machines, laden with mechanical or electronic sensors, probe the machined part for any anomalies. The sensors are mechanically moved into close proximity with the machined part since the sensors are only accurate close to the part's surface. (In the present system, on the other hand, the active system elements, the transducers and the pickups $4_1 \ldots$, typically are located several wavelengths (e.g., a foot or so) from from the part.) Motion is controlled servomotors or stepper motors similar to the motion control in numerically controlled machine tools; however, a sensor replaces the cutter. As each dimension must be inspected one after another by the sensor, the inspection process for each part is necessarily time consuming. A typical part requiring twenty-five dimensions to be inspected might spend a full minute at an inspection station. Furthermore, these machines are very expensive for automated manufacturing applications where inspection must be done more often than in conventional manufacturing.

Phase monitored inspection is a technique which can greatly increase the speed of automated inspection while simultaneously reducing its cost. The typical part with twenty-five dimensions can be inspected in less than a second with phase monitored inspection. Since automated manufacturing has two distinct inspection tasks (dimension inspecting and gross error inspecting), phase monitored inspection can be built specifically for each of these tasks. A microwave phase monitored inspection system can inspect dimensions to high accuracy while an acoustic phase monitored inspection system is sufficient for gross error inspection. An order of magnitude cost reduction is possible with an acoustic phase monitored inspection system compared to a conventional point-to-point inspection machine. Phase monitored inspection is well suited to automated manufacturing since it easily accepts an arbitrary part shape. No-moving-parts operation reduces maintenance and ensures the long life required in automated factories. Phase monitored inspection is not intrinsically linked to automated manufacturing, as a stand-alone inspection method it is an important advance in the state of the art of automated inspection.

The transducer 5 in FIG. 2 can be a microwave antenna and the elements $4_1 \ldots$ can be microwave receivers. The chamber 6 need not be a closed chamber.

Figure 5:
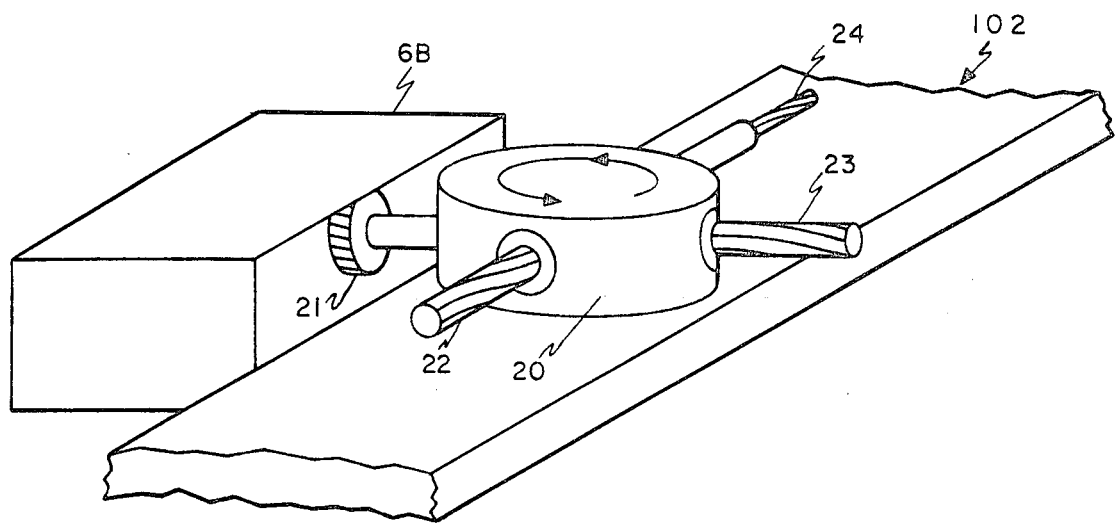
Figure 6:
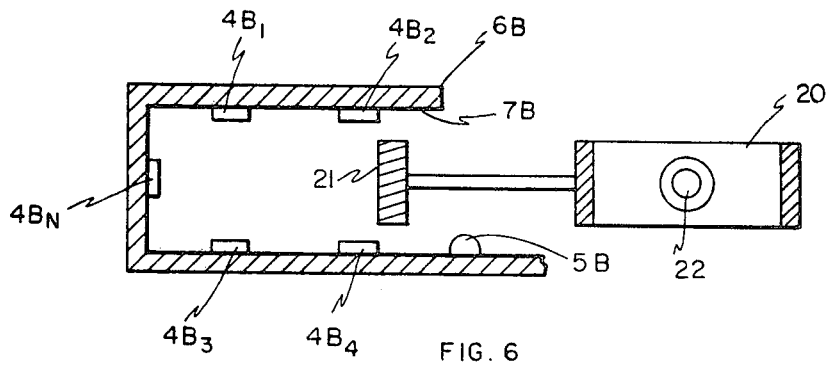
FIG. 6 is a side section view showing some of the elements of FIG. 5.

The system shown at 102 in FIG. 5 is a part of a turret lathe having a turret 20 and cutters or other tools 21, 22, 23 and 24. The system 102 includes a chamber 6B as before and, as best shown in FIG. 6, an emitter 5B and receiver $4B_1 \ldots 4B_N$. The function of the inspection part of the system 102 is to detect differences $\theta_A$ and $\theta_B$ all derived from the same object but at different times so that any change in the geometrical characteristics of the object over time may be detected—to sense wear of the cutting tools $21 \ldots$, for example. The analyzing electronics, analog and digital, can be similar to that shown in FIG. 2.

Figure 7:
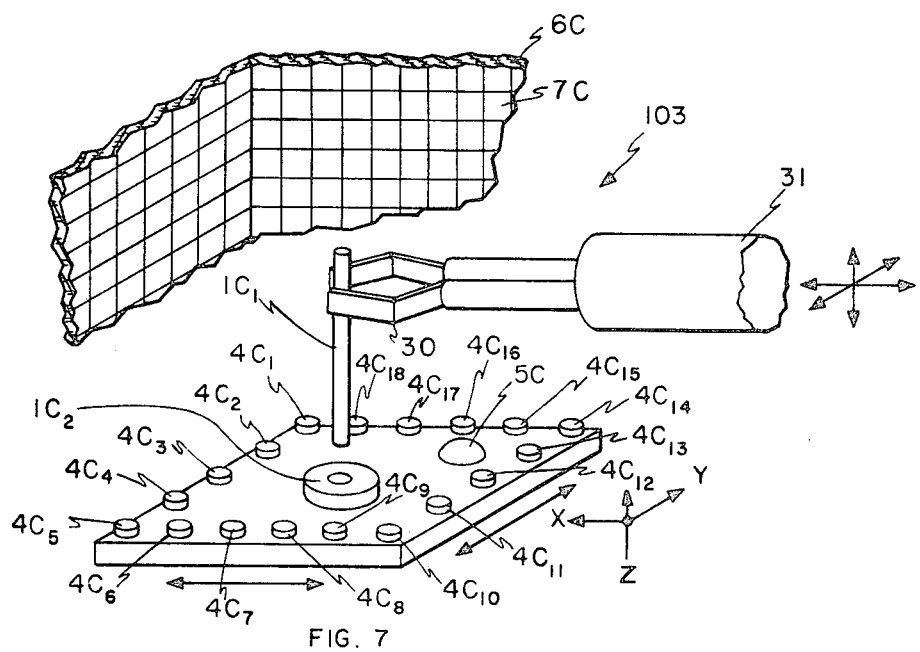
FIG. 7 is an isometric partial view of a system that employs the concepts of the present invention to permit small positional changes in a robot-type device.

The system shown at 103 in FIG. 7 is a part of an automatic assembly system, sometimes called an industrial robot. The duty to be performed in the system 103 is that of fitting a rod $1C_1$ into a central hole in an apertured disk $1C_2$, and the concepts herein disclosed are employed to make final and accurate adjustments of the manipulating hand shown at 30 of an industrial robot 31.

It is assumed that gross initial position changes of the hand 30 can be accomplished by other available apparatus. In the system 103 a wave emitter 5C emits wave energy as before and that wave energy is detected by receivers $4C_1$–$4C_{18}$ and appropriately analyzed. Appropriate feedback circuitry permits small changes to be made in the manipulator hand 30 in the x,y and z directions to effect the required assembly. It will be appreciated that what is being done here is that of positioning the object $1C_1$ relative to the source of wave energy 5C, the disk $1C_2$ and the receivers $4C_1 \ldots$ being in known positions relative to the emitter 5C.

Further modifications of the invention herein described will occur to persons skilled in the art and all such modifications are deemed to be within the spirit and scope of the invention as defined by the appended claims.

What is claimed is:

1. A method that employs geometrical characteristics of an object as a source of information with respect to the object, that comprises: directing wave energy of a single frequency upon the object which reflects the same; detecting the reflected wave energy; comparing a characteristic of the reflected wave energy with the same characteristic of the wave energy directed upon the object to note any difference $\theta_A$ therebetween; and comparing the difference $\theta_A$ with a standard difference $\theta_B$ of the same characteristic to determine any differential $\theta_\Delta$ therebetween, the differences $\theta_A$ and $\theta_B$ being indicative of relative positions between the object and a source of wave energy; said reflected wave energy being detected at a plurality of locations and said difference $\theta_A$ being developed as a plurality of differences $\theta_1'$, $\theta_2' \ldots$, said standard difference $\theta_B$ being a corresponding plurality of differences $\theta_1, \theta_2 \ldots$, differential $\theta_\Delta$ being developed for each corresponding pair to develop data comprising $\theta_1-\theta_1'$, $\theta_2-\theta_2' \ldots$, the data thus developed providing said information.

2. A method as claimed in claim 1 wherein said characteric is the amplitude of the reflected wave energy and the original wave energy and wherein the amplitude of the reflected wave energy is compared with the amplitude of the original wave energy to develop the difference $\theta_\Delta$.

3. A method as claimed in claim 1 wherein the differences $\theta_A$ and $\theta_B$ are derived from the same object but at different times so that any change in the geometrical characteristics of the object over time may be detected.

4. A method as defined in claim 1 in which said characteristic is the phase of the wave energy and wherein the phase of the reflected wave energy is compared with the phase of the wave energy directed upon the object to develop the difference $\theta_A$.

5. Apparatus that comprises, in combination: source means directing wave energy upon an object that reflects the same; means for detecting the reflected wave energy and developing a signal $\theta_A$ therefrom, which signal bears a relationship to geometrical characteristics of the object; and means comparing the signal $\theta_A$ with a standard signal $\theta_B$ representative of the geometrical characteristics of a standard to determine any differential $\theta_\Delta$ therebetween; said means for detecting being operable to detect the reflected wave energy at a plurality of separated locations to provide an array of measurements with respect to the object and to develop a signal $\theta_A$ therefrom as to the wave energy detected at each location of said plurality of locations, which signal $\theta_A$ bears a relationship to the relative positions of the object and the source, said means comparing being operable to compare the signal $\theta_A$ derived from each location with a standard signal $\theta_B$ representative of said relative positions as to the corresponding location to determine any differential $\theta_\Delta$ therebetween with respect to each location to provide an array of differentials $\theta_\Delta$, said means for comparing being operable to combine the array of differentials $\theta_\Delta$ with an array of sensitivities to produce an array of deviations d, each deviation d being produced by a plurality of said differentials $\theta_\Delta$.

* * * * *